United States Patent [19]

Markus et al.

[11] Patent Number: 5,358,861
[45] Date of Patent: Oct. 25, 1994

[54] PROCESS FOR THE PREPARATION OF PHENYLALDEHYDES

[75] Inventors: Paul H. Markus, Loosdrecht; Alfons L. Peters; Robert Roos, both of Bussum, all of Netherlands

[73] Assignee: Unilever Patent Holdings B.V., Vlaardingen, Netherlands

[21] Appl. No.: 973,991

[22] Filed: Nov. 10, 1992

[30] Foreign Application Priority Data

Nov. 11, 1991 [EP] European Pat. Off. ........ 91202920.4

[51] Int. Cl.[5] .......................... C12P 7/24; C12P 1/04; C12R 1/06
[52] U.S. Cl. ..................................... 435/147; 435/189
[58] Field of Search ................................. 435/147, 189

[56] References Cited

U.S. PATENT DOCUMENTS

| | | | |
|---|---|---|---|
| 4,981,795 | 1/1991 | Cooper | 435/147 |
| 5,128,253 | 7/1992 | Labuda et al. | 435/147 |

FOREIGN PATENT DOCUMENTS

| | | | |
|---|---|---|---|
| 0405197 | 1/1991 | European Pat. Off. | 435/147 |
| 0453368 | 10/1991 | European Pat. Off. | 435/147 |

*Primary Examiner*—Herbert J. Lilling
*Attorney, Agent, or Firm*—Cushman, Darby & Cushman

[57] ABSTRACT

A process for the preparation of phenylaldehydes, in particular vanillin by converting compounds having the formula

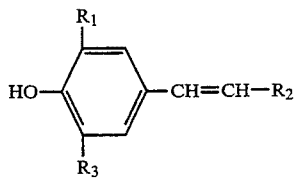

wherein
$R_1 = H$, OH, $OCH_3$ and $C_{1-4}$ alkyl,
$R_3 = H$, OH, $OCH_3$ and $C_{1-4}$ alkyl, and
$R_2 = H$, $C_{1-6}$ alkyl, $-CH_2OH$, $-COOH$, $-OCH_3$ and $-CH_2O-R_4$, wherein
$R_4$ = benzoyl or $C_{1-4}$ alkanoyl or
$R_2 = -CO-CH_2-CO-$;

the last radical combining two structures having formula I or its tautomeric isomers in the presence of the enzyme lipoxidase (EC 1.13.11.12) (also called lipoxygenase) into the phenylaldehyde compounds having the formula

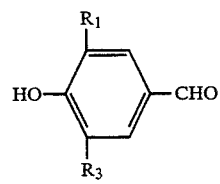

wherein $R_1$ and $R_3$ have the meanings indicated above.

11 Claims, No Drawings

PROCESS FOR THE PREPARATION OF PHENYLALDEHYDES

The invention relates to a process for the enzymatic preparation of phenylaldehydes, in particular vanillin.

Of the group of phenylaldehydes vanillin is the most important flavouring compound for foodstuffs. This compound may be produced by extracting the pods or beans of *Vanilla planifolia* with for instance ethanol. However, performing such a production process on an industrial scale is not considered attractive on account of the high production costs of vanillin. For that reason the major amount of vanillin is made in a "synthetical" way e.g. lignine oxidation and by the oxidation of eugenol or iso-eugenol.

In view of the last-mentioned process it is pointed at EP-A 405,197 directed to a process for the preparation of vanillin. According to this EP-A vanillin may be prepared by a microbial conversion of eugenol and/or isoeugenol by means of strains belonging to the genera Serratia, Klebsiella and Enterobacter.

Applicant has repeated the process of EP-A 405,197, however, no reproduction of the results was possible, probably due to substrate toxicity of e.g. isoeugenol; see in this respect also column 3, lines 29–31 of said EP-A 405,197 reading: "For the protection of the microorganisms against the toxic activity of the eugenol and isoeugenol...". W. -R. Abraham et al in "Bioflavour '87", Proceedings of the International Conference in Würzburg, Sep. 29–30, 1987 describe the synthesis of vanillin from eugenol by several fungi and bacteria, again with low yield.

In view of the great importance of the phenylaldehyde vanillin there is a need for an adequate method for producing vanillin by a microbial or enzymatic process. Surprisingly it has been found that phenylaldehydes i.e. also vanillin may be prepared by converting starting compounds having formula (I)

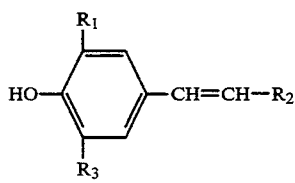

wherein
$R_1$=H, OH, OCH$_3$ and C$_{1-4}$ alkyl,
$R_3$=H, OH, OCH$_3$ and C$_{1-4}$ alkyl, and
$R_2$=H, C$_{1-6}$ alkyl, —CH$_2$OH, —COOH, —OCH$_3$ and CH$_2$O—R$_4$ wherein
$R_4$=benzoyl and C$_{1-4}$ alkanoyl or
$R_2$=—CO—CH$_2$—CO—(I), thus combining two groups having formula I;

or the tautomeric isomers of formula I in the presence of the enzyme lipoxidase (EC 1.13.11.12) (also called lipoxygenase) resulting in the corresponding compounds having formula

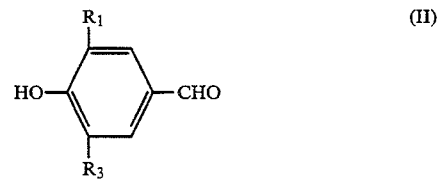

wherein $R_1$ and $R_3$ have the meanings indicated above. Preferably one of the symbols $R_1$ and $R_3$ represents a hydrogen atom whereas the other symbol $R_1$ or $R_3$ represents a methoxy group in which case the end product will be vanillin.

The above-identified compounds having formula I which are suitable as starting compounds in the process of the invention should preferably be obtained from natural sources. Examples of such suitable precursors are:

iso-eugenol (compound having formula I, wherein $R_1$=H, $R_2$=CH$_3$ and $R_3$=OCH$_3$); a constituent of a.o. ylang ylang oil, champaca oil and nutmeg oil. (The Essential Oils, Vol. II, page 521).

eugenol, the tautomeric isomer of iso-eugenol; eugenol is a constituent of e.g. clove bud oil and clove leaf oil;

coniferylalcohol (compound having formula I, wherein $R_1$=H, $R_2$=CH$_2$OH and $R_3$=OCH$_3$); this compound is present in hydrolysed benzoe resin products and products obtained therefrom (Sumatra benzoe resin, Siam benzoe resin etc.); and coniferyl benzoate (compound having formula I, wherein $R_1$=H, $R_2$=—CH$_2$—O—CO—C$_6$H$_5$ and $R_3$=OCH$_3$); this compound is present in benzoe products (see above);

With regard to the enzyme lipoxidase it is brought to the fore that this enzyme is known from the prior art. For instance, in the book Enzymatic Reaction Mechanisms of C. Walsh, (1979), pp.520–521 the introduction of both atoms of O$_2$ as a peroxy group at one terminus of a cis-1,4-diene system under the influence of soy bean lipoxidase is mentioned. Further in J. Biochem. Vol.15, no. 11, pp. 1295–1304 (1983) a recovery method for lipoxidase from Baker's yeast is disclosed. The enzyme activity ratio being 50:50 is based on the reaction of the lipoxidase with linoleic acid resulting in 9- and 13-LOOH isomers (9- and 13-hydroperoxides).

As already indicated in the above J. Biochem. reference lipoxidase (EC.1.13.11.12) is widely distributed in plants. Therefore this enzyme has been isolated from various plants and characterized as indicated in Table A below.

TABLE A

| Source | pH Opt. |
|---|---|
| Bakers yeast | 6.3 |
| Apple | 6.9 |
| Cotton | 6.0–6.5 |
| Cucumber | 5.5 |
| Rice germ | 4–7 |
| Tea leaf | — |
| Grape | 8 |
| Gooseberry | 6.5 |
| potato | 5.5 |

Further the enzyme lipoxidase is present in several microorganisms like strains of the genera Saccharomyces, for instance *Saccharomyces cereviseae* and Fusarium, for instance *Fusarium oxysporum*. Therefore the process according to the invention may also be carried out with this type of microorganisms instead of the isolated enzyme lipoxidase.

The enzyme lipoxidase is also marketed as a commercial product like the lipoxidase extracted from soy bean (Supplier: Sigma No. L 8383).

The enzymatic conversion of the above-identified precursor according to the invention may be carried out in a pH-range of 4–10, being dependent on the lipoxidase used; (see for instance above Table A). However, preferably a commercial lipoxidase like soy bean lipoxidase (Supplier Sigma, No. L8383) is used having an optimum pH-value of about 8. With respect to the optimum pH-value for each type of lipoxidase enzyme the use of a buffer for maintaining the pH-value in question is considered desirable. For that reason a buffer like a borate buffer or a pH-controller may be applied in the process according to the invention.

The amount of lipoxidase added to the substrate may vary within wide limits, for instance in the range of 0.01–20% w/w, preferably 0.1–5 w/w based on the substrate. The substrate concentration in the reaction broth depends on the substrate used but will normally vary between 10 and 250 g/l. The incubation time of the lipoxidase may vary from several hours up to several days dependent on the way of performing the conversion of the substrate. Further, the reaction may be carried out in reaction vessels, provided with a means for agitating the reaction mixture e.g. by stirring, shaking and/or a means for bubbling a gas through the mixture.

According to a specific embodiment of the invention an amount of oxygen, preferably in the form of air may be bubbled through the reaction mixture. In this respect it is brought to the fore that oxygen is obligatory for the bioconversion according to the invention. The reaction should be carried out between 5 and 100% of the saturation concentration of oxygen in the medium, preferably between 50 and 100%.

The temperature of the reaction according to the invention depends on the temperature/activity-range of the lipoxidase enzyme in question, and is for most enzymes between 10° and 40° C., preferably about 20°–30° C.

Further the enzymatic conversion according to the invention is carried out in a solvent, preferably a "food grade" solvent. This term "food grade" solvent encompasses the following group of permissible solvents:
a) water
b) food substances which possess solvent properties (for instance fatty oils like olive oil, sunflower oil, peanut oil, corn oil etc.); and
c) solvents authorized as carrier solvents for flavourings, i.e. propane, butane, butyl acetate, ethyl acetate, ethanol, carbon dioxide, acetone, nitrous oxide, diethyl ether, isobutane, hexane, cyclohexane, methyl acetate, butan-1-ol, butan-2-ol, ethylmethylketone, dichloromethane, methyl-propane-1-ol, glycerol and propylene glycol.

The endproduct of the process according to the invention i.e. the phenylaldehydes like vanillin may be recovered from the crude reaction mixture in a usual way, for instance by extracting the prepared phenylaldehyde from the reaction mixture and subsequently removing the extraction agent by for instance evaporation.

The phenylaldehyde products according to the invention may be used successfully in perfume compositions and in articles and materials to be perfumed.

The phrase "perfume composition" means a mixture consisting of fragrances and optionally auxiliary substances which may be dissolved in an appropriate solvent or mixed with a powdery substrate and used to impart a desired odour to the skin and/or various products. Such perfume compositions as well as the compounds according to the invention per se may be used for perfuming of products. Examples of such perfumed products are: soap, shower and bath products, washing agents, dish washing and cleaning agents, air fresheners and room sprays, pommanders, candles, cosmetics such as creams, ointments, lotions, colognes, pre- and after shave lotions, talcum powders, hair care agents, body deodorants and anti-perspirants.

Fragrances and mixtures thereof which in combination with the phenylaldehyde products according to the invention can be used for the preparation of perfume compositions are e.g. naturally occurring products such as essential oils, absolutes, resinoids, resins, etc., especially synthetic fragrances, such as hydrocarbons, alcohols, aldehydes, ketones, ethers, acids, esters, acetals, ketals, nitriles etc., covering saturated and unsaturated compounds, aliphatic, carbocyclic and heterocyclic compounds.

Examples of fragrances which may be used in combination with the compounds according to the invention are: geraniol, geranyl acetate, linalool, linalyl acetate, tetrahydrolinalool, citronellol, citronellyl acetate, dihydro myrcenol, dihydro myrcenyl acetate, tetrahydro myrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloro-methylphenylcarbinyl acetate, p-tert. butylcyclohexyl acetate, isononyl acetate, vetiveryl acetate, vetiverol, α-hexylcinnamaldehyde, 2-methyl-3-(p-tert.butylphenyl)-propanal, 2-methyl-3-(p-isopropyl phenyl)-propanal, 3-(p-tert.butylphenyl)propanal, tricyclodecenyl acetate, tricyclodecenyl propionate, 4-(4-hydroxy-4-methylpentyl)3-cyclohexene carbaldehyde, 4-(4-methyl-3-pentenyl)-3-cyclohexene carbaldehyde, 4-acetoxy-3-pentyl-tetrahydropyran, 3-carboxymethyl-2-pentyl-cyclopentane, 2-n-heptylcyclopentanone, 3-methyl-2-pentyl-2-cyclopentanone, n-decanal, n-dodecanal, dec-9-en-1-ol, phenoxy-ethyl isobutyrate, phenylacetaldehyde dimethylacetal, phenyl-acetaldehyde diethylacetal, geranyl nitrile, citronellyl nitrile, cedryl acetate, 3-isocamphyl cyclohexanol, cedrylmethyl ether, isolongifolanon, aubepine nitrile, aubepine, heliotropine, coumarin, eugenol, vanillin, diphenyl oxide, hydroxy citronellal, ionones, methyl ionones, isomethyl ionones, itrones, cis-3-hexenol and esters thereof, indan musk fragrances, tetralin musk fragrances, isochroman .musk fragrances, macrocyclic ketones, macrolactone musk fragrances, ethylene brassylate, aromatic nitromusk fragrances.

Auxiliary agents and solvents which may be incorporated into perfume compositions containing a phenylaldehyde product according to the invention are e.g. ethanol, isopropanol, diethyleneglycol monoethylether, diethylphthalate etc.

The amount of the phenylaldehyde products according to the invention, in particular vanillin that can be used in a perfume composition or in a perfumed product can be varied within broad limits and depends e.g. on the product wherein the fragrance is used, the nature and the amount of the further components of the perfume composition and the odour effect desired. Therefore, it is only possible to indicate very broad limits, which give, however, a person skilled in the art sufficient information for an independant use of the compounds according to the invention. In most cases a quantity of only 0.01% by weight in a perfume composition is sufficient to obtain a clearly observable odour effect. On the other hand for obtaining special odour effects it is possible to use a quantity of 1% or more in a composition.

In products perfumed with the aid of perfume compositions according to the invention the concentration is proportionally lower and depends on the quantity of the composition used in the product.

The phenylaldehyde products obtained by the process according to the invention may also be added to flavour compositions or food-stuffs, for instance bakery products, chocolats, ice-cream desserts and other dairy products like margarines and cheese. Flavouring components which may be used together with the phenylaldehyde products according to the invention are well known in the art and are mentioned, e.g., in S. Arctander, Perfume and Flavor Materials of Natural Origin (Elisabeth, N.J., USA, 1969), in T.E. Furia et al., CRC Fenaroli's Handbook of Flavor Ingredients, 2nd Ed. (Cleveland, CRC Press Inc., 1975) and in H.B. Heath, Source Book of Flavors (The Avi Publishing Company Inc., Westport, Conn. 1981).

The invention will be illustrated with the following examples which, however, may not be interpreted in a restrictive way.

EXAMPLE 1

On the basis of the substrates (a) Benzoe Siam Resin (b) isoeugenol and (c) eugenol, all dispersed in tap water as the reaction medium, the compound vanillin was produced. The substrates were taken up in flasks mounted on a shaking apparatus after which the enzyme lipoxidase (Sigma L8383) in a dose of 0.2% w/w based on the substrate was added. The temperature during the reaction was kept at 25° C. The starting mixture had a initial pH of 8. After an incubation time of 24 hours the reaction was stopped by inactivation of the enzyme (10 min. at 70° C.). The results of the experiments are shown in Table B below.

TABLE B

| Substrate | Intake (substrate) g/l | Yield (vanillin) g/l | Conversion (molar) % |
|---|---|---|---|
| Benzoe Siam Resin (70% of coniferyl benzoate) | 50 | 2–4 | 10–20 |
| Isoeugenol | 100 | 10–15 | 10–15 |
| Eugenol | 100 | 0.3–0.5 | 0.3–0.5 |

EXAMPLE 2

100 ml of water was adjusted to a pH of 9 by adding a sufficient amount of 10% w/w NaOH solution. Then 17 mg of lipoxidase (Sigma L8383) and 50 mg of grounded Benzoe Siam resin were added to above mentioned solution. A dispersion was made in 10 seconds by means of a blender (Waring). The dispersion was shaken for 3 days in a shaken incubator (Gallenkamp) at 150 rpm and 25° C. A vanillin concentration of 0.1 mg/ml was determined by means of a HPLC (=High Performance Liquid Chromatography)-analysis.

The dispersion was adjusted to a pH of 3 with 3% w/w HCl and extracted 5 times with 20% v/v diethylether (Merck 921) in a separator funnel. The collected ether layers were dried over MgSO4 and the solvent was evaporated under atmospheric pressure in a Widmer column till a volume of 1 ml was reached. In this product 4 mg of vanillin could be determined (GC-MS =Gaschromatography-mass Spectrometry) analysis.

EXAMPLE 3

In accordance with Example 2 a dispersion of 5 gram of resin and 1 gram of lipoxidase (Sigma L8383) was made in 100 ml of water having a pH of 9. The obtained dispersion was put in an aeration vessel, through which air was bubbled at a rate of 30 l/hr. After 24 hours a vanillin concentration of 2 g/l was determined with HPLC-analysis. The isolation was carried out in accordance to Example 2. After the evaporation step 1.3 g of product was obtained containing 180 mg of vanillin.

EXAMPLE 4

In accordance to Example 2 a dispersion of 50 g of resin in 1.2 liter of water was made having a pH of 8. The obtained dispersion was put in a reactor. The pH was kept at a value of 8 by means of a pH-controller; a 2N NaOH solution was used for this purpose. Under stirring (200 rpm) 1 g of lipoxidase (Sigma L8383) was added. Then the air supply was adjusted to 7.5 l/hr. A vanillin concentration of 0.9 g/l was determined by HPLC-analysis.

EXAMPLE 5

20 g of boric acid (Merck 165) was dissolved in 1 kg of water under stirring. Then the pH was adjusted to the value of 8 with the help of 10% w/w NaOH solution. Further a 35% w/w solution of Benzoe Siam resin was made in ethanol. 75 ml of this resin solution was added dropwise under stirring (Waring Blender) to 500 ml of the above indicated buffer. Subsequently 500 mg of lipoxidase (Sigma L8383) was added thereto under quick stirring. As disclosed in Example 2 the obtained dispersion was shaken. After 7 days a vanillin content of 1.2 g/l was determined by GC-analysis.

EXAMPLE 6

20 g of NaOH was dissolved in 3 liter of water. Then such an amount of boric acid was dissolved as necessary for adjusting the pH to 8.8. Thereupon 2.5 g of lipoxidase (Sigma L8383) was dissolved in the obtained buffer solution.

Further 120 g of Benzoe Siam resin was dissolved in 60 ml of ethanol at a temperature of 50° C.

The enzyme solution was put in a reactor, saturated with air and brought at a temperature of 25° C. The resin solution was added dropwise to the enzyme solution in about 30 min. under stirring (500 rpm). After the addition of the resin solution the stirring speed was increased to 1000 rpm; the pH decreased quickly to a value of 7.

After 4 hours the reactor was emptied. The insoluble material was filtered over a paper filter. The filtrate was acidified with 3% w/w HCl to a pH-value of 3 and extracted 5 times with 10% v/v ether. The isolation took place as in Example 2. Finally 30 g of product was obtained comprising 6 g of vanillin, determined by GC-analysis.

EXAMPLE 7

Two mixtures consisting of 25 ml of isoeugenol in 25 ml of water were made. The pH-values of the two mixtures were adjusted to 7 and 8 respectively by means of a 1N NaOH solution under stirring. After the adjustment of the pH-values 50 mg of lipoxidase (Sigma L8383) was added to each mixture. Within four days in both mixtures the pH was decreased to a value of 5.5. The following vanillin contents were determined by GC-analysis and HPLC-analysis: solution having an initial pH-value of 7: 17 g/l of vanillin; solution having an initial pH-value of 8:22.8 g/l of vanillin.

EXAMPLE 8

3 liters of water was adjusted to a pH-value of 8.5 with a 10% NaOH solution. 10 ml of this water was used for dissolving 300 mg of lipoxidase (Sigma L8383) therein. After 30 min. the enzyme solution was added to the remaining water having a pH-value of 8.5. The enzyme solution obtained in this way was put in the reactor. The pH was kept constant by means of a pH-controller. 150 g of isoeugenol was added under stirring. The reactor was used under the following conditions:

| Start volume | 3 liters |
|---|---|
| Air supply | 42 l/h |
| Stirring speed | 400 rpm |
| pH | 8.5 |
| Temperature | 25° C. |

After 80 min. a vanillin content of 2.1 g/l was determined by GC-analysis; after 120 hours a vanillin content of 7.3 g/l was determined by GC-analysis.

EXAMPLE 9

4 liters of water was added to 600 g of full-cream Soja flakes (untoasted). After 1 hour the obtained broth was pressed through a cheese cloth. 3.2 liters of a crude enzyme solution was obtained. Then the obtained solution was centrifuged for 60 min. at 4000 ×g and at 10° C. for separating the major part of the fat and flour rests. 3 liters of enzyme solution was obtained which was ready for use.

The extract was put in a reactor; the rest of the process was carried out analoguous to Example 8. After 48 hours a vanillin concentration of 4.3 g/l was determined by GC-analysis.

EXAMPLE 10

The process was carried out in accordance with Example 7, however, with eugenol as starting material. After 4 days the final pH was 7.0 in both mixtures.

The following vanillin contents were determined by GC-analysis and HPLC-analysis:
   solution having an initial pH-value of 7:0.3 g/l of vanillin;
   solution having an initial pH-value of 8:0.5 g/l of vanillin.

EXAMPLE 11

In accordance with Example 5 a borate buffer having a pH of 9 was prepared. 20 mg of lipoxidase (Sigma L8383) was added to 200 ml of the above-identified buffer. After solubilisation of the enzyme 10 g of Anol (4-(1-propenyl)phenol) was added. The emulsion was shaken for 50 hours in the shaking incubator (Gallenkamp) at 150 rpm and 25° C. A p-hydroxybenzaldehyde content of 14.3 g/l was determined (GC-analysis).

EXAMPLE 12

The process was carried out in accordance with Example 11, however, the starting material Anol was replaced by Chavicol (4-(2propenyl)phenol). A p-hydroxybenzaldehyde content of 9 g/l was determined (GC-analysis).

EXAMPLE 13

1 liter of sterilized (20 min. at 121° C.) culture medium, present in a fermentor (Applicon, Schiedam, Holland) and consisting of 1% w/w glycerol, 0.3% w/w $Na_2HPO_4$, 0.25% w/w $KH_2PO_4$, 0.25% w/w $(NH_4)_2/SO_4$, 0.05% w/w yeast extract (Difco), 0.05% w/w $MgSO_4.7H_2O$, 0.003% w/w $CaCl_2.2H_{20}$ and 0.0025% w/w $FeSO_{4.7}H_{20}$, was inoculated with 4.10E4 viable cells of *Saccharomyces cerevisiae* (Kitzinger Reinhefe for all purposes). The mixture was agitated at 600 rpm, aerated with 0.1 vvm at a temperature of 25° C. After 20 hours 2 g of isoeugenol was added and 48 hours after the inoculation a vanillin concentration of 189 mg/l was measured in the broth using GLC (=gas liquid chromatography)-analysis.

EXAMPLE 14

Since potato is a suitable source of lipoxydase (H. D. Berkeley and T. Galliard, Phytochem. 15 (1976) pp 1475–1479 and 1481–1484), potaty juice was used for converting isoeugenol into vanillin. Thus 1 kg. of fresh potatoes (variety Desirée) was comminuted and pressed through cheece cloth to obtain 550 g. of potato juice. In each of 5 250 ml shaking flasks 50 g. potato juice was mixed with 5 g. isoeugenol. Each flask was brought to a different pH as indicated in the table below and shaken at room temperature for 19 hours. Samples were taken from each flask at different intervals, again as indicated below and each time a sample was taken, the pH was brought to the original value with concentrated NaOH solution. The vanillin content in each sample is presented in the table below:

| | pH in shaking flask | | | | |
|---|---|---|---|---|---|
| | 6,5 | 7,5 | 8 | 8,5 | 9,5 |
| time(h) | Vanillin content in g/l | | | | |
| 0,5 | 0,54 | 0,10 | 0,067 | 0,064 | 0,014 |
| 3,5 | 2,0 | 2,5 | 2,0 | 1,96 | 1,56 |
| 19 | 5,8 | 6,4 | 2,2 | 2,2 | 1,8 |

EXAMPLE 15

A lipoxydase solution was prepared from defatted soy flour (Provaflor marketed by Vamomills, Bergen op Zoom, The Netherlands) by mixing 1 part of flour with 10 parts of an acetate buffer solution containing 1 g. acetic acid and 2 g. of sodium acetate per liter (pH 5.0). This mixture was stirred for 1 h. at 5° C. and thereafter centrifuged for 15 minutes at 4000×g. The remaining clear lipoxydase solution was used for the preparation of vanillin from isoeugenol as outlined below.

Three batches of 10 l. enzym solution where brought at pH 7.5 (with a 25 g/l phosphate buffer), pH 8 (kept constant with NaOH solution) and pH 8.5 (with a 10 g/l borate buffer) respectively. To each batch 100 g. isoeugenol was added gradually over 4 h. while the batch was kept at 25° C., was stirred at 500 rpm and 0,05 vvm air was bubbled through. On completion of the reaction after 24 h. the reaction mixtures were brought to pH 9 and each extracted with twice the volume of hexane. Evaporation of the hexane solutions obtained led to complete recovery of unused isoeugenol.

The remaining aqueous solutions were acidified to pH 6 and again extracted, now with 10 times the volume of hexane. Evaporation of the hexane solutions yielded 10.1 g, 12 g and 10.2 g. of crude vanillin respectively. This could be purified by recristallization from water.

EXAMPLE 16

Example 15 was repeated with the provise that 4 h. after the start of the reaction 1 l of lipoxidase concentrate was additionally added to each batch. This concentrate was obtained by ultrafiltration of a quantity of the original lipoxidase solution through a 10 k Dalton membrane (Millipore Pellicon cassette system with Filtron filtercassette Omega 10 k). A 10 times concentrated enzyme solution was obtained. After 24 hours the quantities of vanillin obtained where 16.0 g, 19.6 g and 18.0 g respectively.

EXAMPLE 17

A vanilla flavour composition for flavouring pudding, was prepared by mixing the following components:

| | |
|---|---|
| Heliotropin | 3 g |
| Maltol | 0.2 g |
| Dihydro coumarin | 0.1 g |
| Diacetyl | 0.1 g |
| Anisaldehyde | 0.05 g |
| Vanilla extract | 50 g |
| Vanillin (according to example 8) | 33 g |
| Arachid oil up to | 1000 g |

Above flavouring was incorporated in a dessert pudding (standard recipe) in a dose of 2 g per kilo of dessert. The obtained flavour was well balanced and the dessert had an excellent vanilla taste.

EXAMPLE 18

A perfume composition of the type "Lou Lou" was prepared by mixing the following components:

| | |
|---|---|
| Lixetane [Quest International] | 80 g |
| Hexylcinnamicaldehyde | 130 g |
| Methylionon gamma | 80 g |
| Linalool | 60 g |
| Tamarin Base [Firmenich] | 4 g |
| Coriander oil | 2 g |
| Styrax oil | 2 g |
| Linalyl acetate | 40 g |
| Ylang oil | 30 g |
| Lemon oil | 20 g |
| Traseolide [Quest International] | 30 g |
| Lyral [IFF] | 20 g |
| Methylbetanaphtylketon | 5 g |
| Cedramber [IFF] | 6 g |
| Karanal [Quest International] | 2 g |
| Bangalol [Quest International] | 4 g |
| Trirosol | 3 g |
| Dimethyl benzylcarbinylbutyrate | 15 g |
| Coumarin | 65 g |
| Cinnamyl acetate | 2 g |
| Anisyl acetate | 6 g |
| Vanillin (product according to Example 8) | 25 g |
| Lacton C 9 gamma | 3 g |
| Methyl anthranilate | 10 g |
| Heliotropin | 15 g |
| Jasmin AB 523 [Quest International] | 60 g |
| Muguet [Quest International] | 40 g |
| Methyl salisylate | 2 g |
| Phenylethylalcohol | 50 g |
| Amberoxide 10% in dipropylene glycol | 2 g |

-continued

| | |
|---|---|
| Iso Esuper [IFF] | 20 g |
| Damascon alpha [Firmenich] | 4 g |
| Damascon beta [Fermentich] | 4 g |
| Orris oil Nardarome [Quest International] | 2 g |
| Dipropylene glycol till | 1000 g |

We claim:

1. Process for the preparation of phenylaldehyde comprising converting a compound having the formula (I)

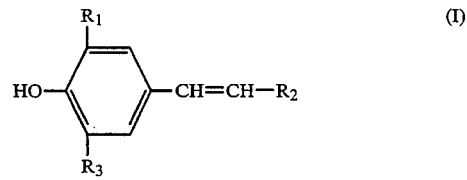

wherein
$R_1$ = H, OH, OCH$_3$ and C$_{1-4}$ alkyl,
$R_3$ = H, OH, OCH$_3$ and C$_{1-4}$ alkyl,
$R_2$ = H, C$_{1-6}$ alkyl, —CH$_2$OH, —COOH, —OCH$_3$ and —CH$_2$O —R$_4$
wherein R$_4$ = benzoyl and C$_{1-4}$ alkanoyl or R$_2$ = —CO—CH$_2$—CO—(I), thus combining two groups having formula I; or the tautomeric isomers of formula I in the presence of the enzyme lipoxidase (E.C. 1.13.11.12), oxygen and a solvent into a phenylaldehyde compound having the formula

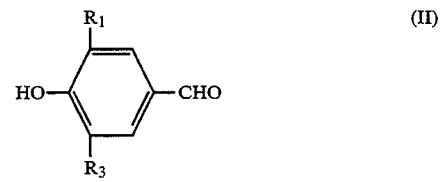

wherein $R_1$ and $R_3$ have the meanings indicated above and recovering the phenylaldehyde compound.

2. Process according to claim 1, characterized by using a starting compound having formula (I) wherein $R_1$ = OCH$_3$, $R_3$ = H and $R_2$ has the meanings indicated in claim 1 or a product containing this starting compound.

3. Process according to claim 2, characterized by using a starting compound having formula I wherein $R_1$ = OCH$_3$, $R_2$ = —CH$_2$O—CO—C$_6$H$_5$ and $R_3$ = H or a product containing this starting compound.

4. Process according to claim 1, characterized by performing the reaction in a "food-grade" solvent.

5. Process according to claim 4, characterized in that the "food-grade" solvent is water.

6. Process according to claim 5, characterized by performing the reaction in an aqueous dispersion having a pH-value in the range of 4–10.

7. Process according to claim 1, characterized by using a lipoxidase enzyme in an amount of 0.01–20% w/w based on the substrate.

8. Process according to claim 1, characterized by using a lipoxidase enzyme, extracted from soy beans.

9. Process according to claim 1, characterized by performing the reaction at an oxygen concentration between 5 and 100% of the saturation concentration of oxygen in the medium.

10. Process according to claim 9, characterized by bubbling air through the reaction mixture.

11. Process according to claim 1, characterized by performing the reaction at a temperature in the range of 20°–30° C.

* * * * *